(12) United States Patent
Trivikram.

(10) Patent No.: US 11,642,479 B2
(45) Date of Patent: May 9, 2023

(54) RESPIRATORY SYSTEM

(71) Applicant: Trivikram., Karnataka (IN)

(72) Inventor: Trivikram., Karnataka (IN)

(*) Notice: Subject to any disclaimer, the term of this patent is extended or adjusted under 35 U.S.C. 154(b) by 352 days.

(21) Appl. No.: 16/606,714

(22) PCT Filed: Mar. 26, 2018

(86) PCT No.: PCT/IB2018/052035
§ 371 (c)(1),
(2) Date: Oct. 18, 2019

(87) PCT Pub. No.: WO2018/178841
PCT Pub. Date: Oct. 4, 2018

(65) Prior Publication Data
US 2021/0290876 A1   Sep. 23, 2021

(30) Foreign Application Priority Data

Mar. 31, 2017 (IN) .............................. 201741011674

(51) Int. Cl.
*A61M 16/00* (2006.01)
*A61M 16/20* (2006.01)
(Continued)

(52) U.S. Cl.
CPC ...... *A61M 16/022* (2017.08); *A61M 16/0006* (2014.02); *A61M 16/0009* (2014.02);
(Continued)

(58) Field of Classification Search
CPC ............ A61M 16/022; A61M 16/0006; A61M 16/0009; A61M 16/20; A61M 16/202;
(Continued)

(56) References Cited

U.S. PATENT DOCUMENTS 3,777,742 A   12/1973  Aumiller et al.
5,014,748 A * 5/1991  Nogami .................. F16K 3/085
                                                    137/625.21
(Continued)

OTHER PUBLICATIONS

International Search Report issued in International Patent Application No. PCT/IB2018/052035, dated Nov. 9, 2018.
(Continued)

*Primary Examiner* — Joseph D. Boecker
*Assistant Examiner* — Thomas W Greig
(74) *Attorney, Agent, or Firm* — Knobbe, Martens, Olson & Bear LLP

(57) ABSTRACT

A respiratory system, primarily to provide a mechanical insufflation/exsufflation therapy, may include a first pressure generating source, a second pressure generating source and a primary valve to switch between insufflation/positive pressure flow and exsufflation/negative pressure flow, and to generate oscillations alongside either of these cycles. The respiratory system can optionally employ a secondary valve either on a fluidic path of the first pressure generating source or on a fluidic path of the second pressure generating source. An interfacing assembly acts as a fluidic conduit between the pressure generating sources and the patient. A control unit is configured to generate required pressurized flow and oscillations as per the user settings. The aforesaid valves can be manipulated into multiple orientations/positions, which are aligned and/or adjusted with respect to the respective pressure generating sources as per the therapy requirements.

21 Claims, 10 Drawing Sheets

(51) Int. Cl.
*A61M 16/06* (2006.01)
*A61M 16/08* (2006.01)

(52) U.S. Cl.
CPC ........ *A61M 16/06* (2013.01); *A61M 16/0875* (2013.01); *A61M 16/202* (2014.02); *A61M 16/0063* (2014.02); *A61M 16/0066* (2013.01)

(58) Field of Classification Search
CPC .............. A61M 16/06; A61M 16/0875; A61M 16/0096; A61M 16/0066; A61M 16/04; A61M 16/204; A61M 16/205; F16K 11/074
See application file for complete search history.

(56) References Cited

U.S. PATENT DOCUMENTS

| | | | | |
|---|---|---|---|---|
| 6,209,540 | B1* | 4/2001 | Sugiura | A61M 16/0006 128/204.18 |
| 2003/0051729 | A1 | 3/2003 | Be'eri et al. | |
| 2006/0036199 | A1* | 2/2006 | Warwick | A61H 31/00 601/44 |
| 2012/0285460 | A1* | 11/2012 | Smith | A61M 16/0006 128/205.24 |
| 2013/0220325 | A1 | 8/2013 | Davis et al. | |
| 2014/0290659 | A1* | 10/2014 | Chen | A61M 16/202 128/205.24 |
| 2015/0027444 | A1* | 1/2015 | Col, Jr. | A61M 16/0009 128/204.21 |
| 2016/0001033 | A1 | 1/2016 | Van De Ven | |
| 2016/0151232 | A1* | 6/2016 | Clapp | A61H 9/0078 601/148 |
| 2017/0027813 | A1* | 2/2017 | Bobey | A61M 16/0009 |
| 2017/0361058 | A1* | 12/2017 | Gaw | A61M 16/0463 |
| 2017/0368410 | A1* | 12/2017 | Brand | A61B 5/0823 |
| 2018/0085541 | A1* | 3/2018 | Ye | A61M 16/0833 |

OTHER PUBLICATIONS

Written Opinion issued in International Patent Application No. PCT/IB2018/052035, dated Nov. 9, 2018.
International Preliminary Report on Patentability issued in International Patent Application No. PCT/IB2018/052035, dated Oct. 1, 2019.

* cited by examiner

Rotary Valve with 2 openings

RESPIRATORY SYSTEM

This application is the U.S. National Phase under 35 U.S.C. § 371 of International Application PCT/ib2018/052035, filed Mar. 26, 2018, designating the U.S., and published in English as WO 2018/178841 on Oct. 4, 2018 which claims priority to Indian Patent Application No. 201741011674, filed Mar. 31, 2017, the entire contents of each of which are incorporated herein by reference.

TECHNICAL FIELD

The present subject matter relates to a medical device in general, and in particular, the present invention relates to mechanical inexsufflation respiratory device which assists in the removal of secretions from patient airways.

BACKGROUND

Patients having lung related diseases are unable to ventilate their lungs properly and may also suffer mucus clearance issues. This may happen when the normal lung defense system is damaged by lung related diseases.

Many patients with neuromuscular weakness, spinal cord injury, as well as many other disorders associated with inability to control the full inhalation and explosive exhalation require mechanical assistance to cough or to remove their lung secretions.

Generally, patients who have neuromuscular issues such as ineffective glottis closure, impaired diaphragm movement or weak respiratory muscles need mechanical assisted cough devices, i.e. Mechanical Insufflation/Exsufflation (M-IE). One of the well-known treatment modalities to treat these kind of patients is Mechanical insufflation and exsufflation device, which is well documented in prior art. For example, M-IE devices mimic/simulate the cough function, typically, for those patients who have a peak airflow lesser than 270 liters per minute, by providing a positive pressure air and suddenly creating a negative pressure inside the lung, which in turn brings the mucus along the upper airways. M-IE devices may also find their application in patients who have upper airway clearance issues after surgery, for example.

In general, the existing secretion clearance devices provide an internal gas source as either internal blowers, turbines or some form of pumps.

Out of the aforesaid devices, dual limb ventilation devices provide a patient circuit which has a dedicated limb for inspiratory gases or the gases going towards the lung and expiratory gases coming out of the lung. Such devices provide an internal positive pressure source while the expiration phase from the lung or external load is passive i.e. flow is generated by recoil of elastic lung and chest wall.

International application WO2007054829 A2 discloses a mechanical in-exsufflation device, comprising a patient interface unit configured to permit a negative pressure airflow therethrough and a positive pressure airflow from a medical mechanical ventilator; a suction unit for generating airflow under negative pressure that flows through the patient interface unit; a first valve for selectively blocking airflow from a medical mechanical ventilator to the patient interface unit; and a second valve separate from the first valve for selectively blocking airflow from the patient interface unit to the suction unit.

Further, a device known and used in the prior art for performing mechanical inexsufflation is the "CoughAssist®" from the JH Emerson Company of Cambridge, Mass. The CoughAssist® device uses a turbine to perform insufflation of the lungs by blowing air into a patient at a defined pressure for a predetermined period of time through a tube connected to the patient's endotracheal tube, tracheostomy tube or facemask. After the predetermined period of time, a valve mechanism within the CoughAssist® device rapidly switches the direction of airflow within the length of tubing, resulting in rapid exsufflation of the patient's lungs. The exsufflation flow continues until the valve mechanism disconnects the tubing from the turbine, terminating the exsufflation flow. There is then a pause period, during which no airflow occurs and airway pressure is equal to zero (atmospheric pressure), until the next insufflation cycle commences. This pause period is necessary to avoid hyperventilation of the patient, and usually lasts about one to three seconds. The cycle is repeated several times to complete the secretion removal treatment. Further, the CoughAssist® device and other such available devices are unable to generate a range of oscillations in combination with the insufflation/exsufflation cycles.

Hence, there is a need for a respiratory system which overcomes the aforementioned and other related challenges.

SUMMARY

It is an object of the present subject matter to provide a multitude of functions to clear patient's airway clearance.

It is another object of the present subject matter to provide a positive pressure generating source.

It is yet another object of the present subject matter to provide a negative pressure generating source.

It is yet another object of the present subject matter to provide a primary valve to allow or block positive and negative airflow to a patient through an interfacing assembly.

It is yet another object of the present subject matter to provide a two-opening rotary valve in fluid connection with the first pressure generating source and the second pressure generating source.

It is yet another object of the present subject matter to provide a three-opening rotary valve in fluid connection with the first pressure generating source and the second pressure generating source.

It is yet another object of the present subject matter to provide a voice coil based valve in fluid connection with the first pressure generating source and the second pressure generating source.

It is yet another object of the present subject matter to provide mechanical insufflation/exsufflation.

The respiratory system comprises a patient interface unit configured to permit either a negative pressure airflow or a positive pressure airflow to a patient interface, a negative pressure generating source for generating negative pressure airflow that flows through the patient interface unit, a positive pressure generating source for generating positive pressure airflow that flows through the patient interface unit and a first valve fluidly connected to said pressure generating sources for selectively blocking and/or unblocking airflow from either of the said pressure generating sources.

In an embodiment of the present subject matter, said first valve is a rotary valve. The first valve, at a first position, is configured to block negative pressurized airflow at patient interface and allows the positive pressurized airflow to enter the patient interface. The first valve, at a second position, is configured to block the positive pressurized airflow at patient interface and allows the negative pressurized airflow to enter the patient interface. The first valve at a third position, with a variable displacement from said third position configured to impart oscillations on top of positive pressure airflow. The first valve at a fourth position, with a variable displacement from said fourth position configured to impart oscillations on top of negative pressure airflow.

The pressure generating sources are connected to the patient interface unit by a tubing, wherein the tubing is a Y shaped tubing. The first valve comprises at least two or more openings of equal or varying sizes. The positive pressure generating source overlaps with either of the said openings to allow positive air flow at the patient interface. The negative pressure generating source overlaps with either of the said openings to allow negative air flow at the patient interface. The first valve is placed inside the respiratory system. The respiratory system further comprises a control unit to control operation of the said system. The control system is configured to generate insufflation and exsufflation waveforms by only operating the said first valve. The control system is further configured to generate oscillations on top of insufflation and exsufflation cycles, one at a time, by only operating the said first valve. The pressure generating sources are one or more of blowers, compressors.

In an embodiment, the first valve is a linear motion valve, wherein the first valve comprises a voice coil having a first plunger and a second plunger. The ends of first and second plungers include a first strip and a second strip respectively. The first strip and the second strip are configured to block the pressure generating sources. The first valve at a first position is configured to block negative pressurized airflow at patient interface and allows the positive pressurized airflow to enter the patient interface. The first valve at a second position is configured to block the positive pressurized airflow at patient interface and allows the negative pressurized airflow to enter the patient interface. The first valve at a third position, with a variable displacement from said third position configured to impart oscillations on top of positive pressure airflow. The first valve at a fourth position, with a variable displacement from said fourth position configured to impart oscillations on top of negative pressure airflow.

A method of performing a mechanical inexsufflation therapy comprises generating positive pressure airflow/insufflation from a positive pressure generating source to the patient's interface/lung through a first valve, the first valve being in first orientation, wherein first position of the first valve selectively prevents negative pressurized airflow at the patient interface/lung, and allows the positive pressure airflow to enter patient interface/lung. Further, generating a negative pressure airflow/exsufflation by using negative pressure generating source 104 along patient interface/lung by using said first valve's second position, wherein second position of the valve selectively prevents positive pressure airflow from entering patient's interface/lung and allows the negative pressure airflow to enter patient interface/lung. Furthermore, the method comprises generating oscillation, either on top of said positive pressure airflow or on top of negative pressure airflow, by back and forth switching of the first valve from third position to fourth position. The step of switching the first valve from first position to second position is based on pre-determined time or pressure or volume parameters. The step of switching the first valve from second position to first position is based on pre-determined time or pressure or volume parameters. The positive pressurized flow ranges from 1 to 100 cmh20 as per the set parameters. The negative pressurized flow ranges from −1 to −100 cmh20 as per the set parameters. The steps of changing the position of the valve, which are optionally automated, is electromechanical in nature. The steps of generating pressurized airflows at the patient interface comprise a defined sequence: positive pressure airflow, followed by positive pressured airflow of higher value, and ends with negative pressure airflow. The step of generating pressurized airflows at the patient interface comprises of a series of said sequence ranging from 1 to 50.

A respiratory system comprises a patient interface unit configured to permit either negative pressure airflow or positive pressure airflow to a patient interface. A negative pressure generating source is provided for generating negative pressure airflow that flows through the patient interface unit. A positive pressure generating source is provided for generating positive pressure airflow that flows through the patient interface unit. A first valve structure fluidly connected to said pressure generating source's airflow paths for selectively blocking and unblocking airflow from either of the said pressure generating sources. A second valve structure fluidly connected to a positive pressure airflow path and/or to a negative pressure airflow path to generate oscillations to said pressurized airflows. The first valve at first position blocks the negative pressure airflow at patient interface and allows the positive pressure airflow to enter the patient interface. The first valve at second position blocks the positive pressure airflow at patient interface and allows the negative pressure airflow to enter the patient interface. The first valve at third orientation with a variable displacement from said third orientation can impart oscillations on top of positive pressure airflow. The first valve at fourth orientation with a variable displacement from said fourth position can impart oscillations on top of negative pressure airflow. The second valve at first position with a variable displacement from said first position can impart oscillations on top of either of pressurized airflow path, depending on the location of the second valve. The second valve structure operationally can change its position from one location to other, either inside the positive pressure path or inside the negative pressure path to generate oscillations on respective pressured airflows.

In an embodiment, the valves are rotary valves. The first position of valve can be a position where the valve can allow complete positive pressurize airflow to pass through it and block the negative pressure airflow from entering the patient interface. The second position of the valve can be a position where the valve can allow negative pressure airflow to pass through it and block the positive pressure airflow from entering the patient interface. The third position of the valve can be any position where the valve can allow complete or partial positive pressure airflow to pass through it and block the negative pressure airflow from entering the patient interface. The fourth position can be any position where the valve can block both positive pressure airflow and negative pressure airflow from patient interface. The fifth position of the valve can be any position where the valve can allow complete or partial negative pressure airflow to pass through it and block the positive pressure airflow from entering the patient interface. The sixth position can be any position where the valve can block both positive pressure airflow and negative pressure airflow from entering the patient interface. The first valve comprises at least two or more openings of equal or varying sizes. The first valve is placed in between the patient interface and second valve. The respiratory system further comprises a control unit to control the operation of the said system. The control system is configured to generate insufflation and exsufflation waveforms by only operating the said first valve.

In an embodiment, the valve is linear valve. The linear motion valve can be made from voice coil. The control system is configured to generate oscillations on top of insufflation and exsufflation cycles, one at time, by only operating the said first valve. The control system is configured to generate oscillations on top of insufflation and exsufflation cycles, both at the same time, by using said two valves. The pressure generating sources are connected to the patient interface unit by a tube. In an embodiment, the tube is a Y-shaped tube.

A method of performing oscillation on top of mechanical inexsufflation therapy comprises: generating pressurized positive airflow/insufflation from a positive pressure generating source to the patient interface/lungs through a first valve, valve being in first position/orientation, wherein first position of the first valve selectively prevents entering negative pressure airflow from entering patient interface/lung. Further, generating a negative pressurized air flow/exsufflation by using negative pressure generating source at patient interface/lung by using said first valve's second position, wherein second position of the valve selectively prevents positive pressure airflow from entering patient lung. Furthermore, generating the oscillation either on top of said positive pressure airflow or on top of said negative pressure airflow by back and forth switching of the first valve from third position to fourth position and simultaneously generating the additional oscillation either of said pressured airflow by back and forth switching of the second valve from one position to other position. The step of switching the first valve from first position to second position is based on pre-determined time or pressure or volume parameters. The step of switching the first valve from second position to first position is based on pre-determined time or pressure or volume parameters. The step of switching the first valve from third position to fourth position and vice-versa is based on pre-determined frequency and oscillation amplitude requirements. The step of switching the first valve from fifth position to sixth position and vice-versa is based on pre-determined frequency and oscillation amplitude requirements. The step of switching the second valve from first position to any other position and vice-versa occurs based on pre-determined frequency and oscillation amplitude requirements. The positive pressurized flow ranges from 1 to 100 cmh20 as per the set parameters. The negative pressurized flow ranges from −1 to −100 cmh20 as per the set parameters. The steps of changing the position of the valve, which are optionally automated, is electromechanical in nature. The steps of generating pressurized flows at the patient interface comprise a defined sequence: positive pressurized flow, followed by positive pressurized airflow of higher value, and end with negative pressurized flow. The defined sequence comprises of a series of said sequence ranging from 1 to 50. The pressure generating sources are one or more of blowers, compressors. The steps of generating oscillation comprises of generating an oscillation of frequency 0 to 50 Hz and amplitude of 1 cmh20 to 100 cmh20. The second valve structure, operationally, can change its position from one location to other, either inside the positive pressure path or inside the negative pressure path to generate oscillations on respective pressured airflows.

BRIEF DESCRIPTION OF ACCOMPANYING DRAWINGS

A further understanding of the present subject matter can be obtained by reference to various embodiments set forth in the illustrations of the accompanying drawings. The drawings are not intended to limit the scope of the present subject matter, which is set forth with particularity in the claims as appended or as subsequently amended, but merely to clarify and exemplify the subject matter.

For a fuller understanding of the nature and object of the present subject matter, reference is made to the accompanying drawings, wherein.

DETAILED DESCRIPTION

Figure 1:
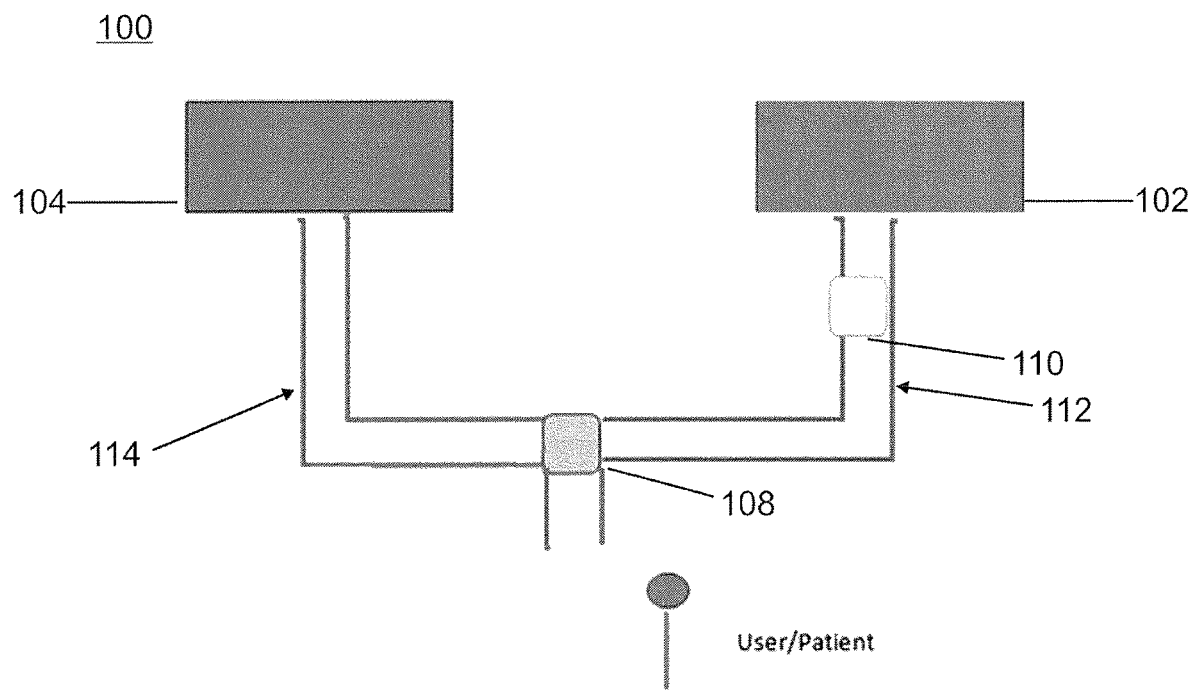
FIG. 1 is a respiratory system in accordance with an embodiment of the present subject matter.

The following presents a detailed description of various embodiments of the present subject matter with reference to the accompanying drawings.

As used herein, the singular forms "a", "an" and "the" are intended to include the plural forms as well, unless expressly stated otherwise. It will be further understood that the terms "includes", "comprises", "including" and/or "comprising" when used in this specification, specify the presence of stated features, integers, steps, operations, elements, and/or components, but do not preclude the presence or addition of one or more other features, integers, steps, operations, elements, components, and/or groups thereof. It will be understood that when an element is referred to as being "connected" or "coupled" to another element, it can be directly connected or coupled to the other element or intervening elements may be present. Furthermore, "connected" or "coupled" as used herein may include operatively connected or coupled. As used herein, the term "and/or" includes any and all combinations and arrangements of one or more of the associated listed items.

The embodiments of the present subject matter are described in detail with reference to the accompanying drawings. However, the present subject matter is not limited to these embodiments which are only provided to explain more clearly the present subject matter to the ordinarily skilled in the art of the present disclosure. In the accompanying drawings, like reference numerals are used to indicate like components.

Unless otherwise defined, all terms (including technical and scientific terms) used herein have the same meaning as commonly understood by one of ordinary skill in the art to which this disclosure pertains. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

The detailed description set forth below in connection with the appended drawings is intended as a description of the several presently contemplated embodiments of a respiratory system. The respiratory system is capable of providing multiple therapies for respiratory system, more specifically, for airway clearance. The apparatus can be configured to deliver various airway clearance therapies through hardware/mechanical, software and patient circuit configurations. This description is not intended to represent the only form in which the disclosed subject matter may be developed or utilized. The description sets forth the functions and features in connection with the illustrated embodiments. It is to be understood, however, that the same or equivalent functions may be accomplished by different embodiments that are also intended to be encompassed within the scope of the present disclosure. It is further understood that the use of relational terms such as first and second and the like are used solely to distinguish one from another entity without necessarily requiring or implying any actual such relationship or order between such entities.

The respiratory system comprises two independent pressure generating sources, a valve to switch between insufflation/positive pressure flow and exsufflation/negative pressure flow, and to generate oscillations on top of either of these cycles. In other words, the valve can be used to generate oscillations along with switching between the insufflation/positive pressure flow and exsufflation/negative pressure flow.

In order to generate secondary oscillations on top on insufflation and exsufflation oscillation cycles, the respiratory system can optionally employ a secondary valve either on a fluidic path of a positive pressure generating source or on a fluidic path of a negative flow generating source. A patient interface unit acts as a fluidic conduit between the pressure generating sources and the patient. A control unit which forms a part of the system is configured to generate required pressurized flow and oscillations as per the user settings. The aforesaid valves can be manipulated into a plurality of orientations/positions, which are aligned and/or adjusted with respect to the respective pressure generating sources as per the therapy requirements.

FIG. 1 illustrates a schematic diagram of a respiratory system 100 in one embodiment of the present disclosure. The respiratory system 100 comprises a plurality of components including but not limiting to a first pressure generating source 102, a second pressure generating source 104 and an interfacing assembly 106. The first pressure generating source 102 and the second pressure generating source 104 are configured to generate flow and pressure. The aforesaid pressure generating sources can be chosen from blowers, turbines, pumps, and the like. However, it is evident to a person of ordinary skills in the art that the type of patient interface tube and the pressure generating sources used does not limit the scope of present disclosure. The interfacing assembly 106 acts as a fluidic conduit between the aforesaid pressure/flow generators and the patient. The respiratory system 100 further includes a primary valve 108 and a control unit. The primary valve 108 is configured to switch between insufflation/positive pressure flow and exsufflation/negative pressure flow, and to generate oscillations in combination with the aforesaid insufflation and exsufflation cycles. A control unit is configured to control the aforesaid pressure generating sources and the primary valve 108 to generate a pressurized flow and oscillation as per the requirement of the user/patient. Further, the respiratory system 100 includes a secondary valve 110 to generate oscillations along with either insufflation or exsufflation. The secondary valve 110 can be positioned in a positive air flow path 112 between the primary valve 108 and the first pressure generating source 102 to generate secondary oscillations during the negative pressure exsufflation cycle. It is to be noted that with said configuration, primary valve 108 can perform dual role, one is to switch between insufflation and exsufflation cycles and other is to generate primary exsufflation oscillations. Alternately, the secondary valve 110 can be positioned in a negative air flow path 114 between the primary valve 108 and the second pressure generating source 104 to generate secondary oscillations during the insufflation cycle. Note that with this configuration, the primary valve can perform dual role, one is to switch between insufflation and exsufflation cycles and other is to generate primary insufflation oscillations.

Figure 2:
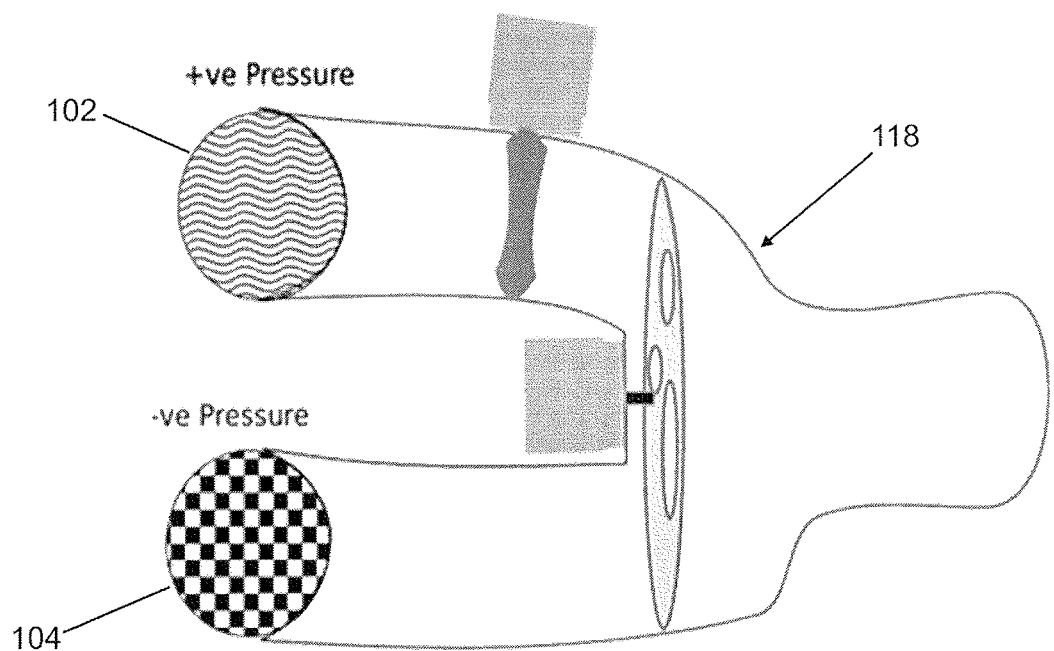
FIG. 2 is a schematic diagram illustrating a respiratory system comprising a rotary valve in accordance with an embodiment of the present subject matter.

In an embodiment, the respiratory system 100 includes a rotary valve comprising a plurality of opening fluidly connected to the first pressure generating source 102 and the negative pressure generating source. FIG. 2 is a schematic diagram illustrating a respiratory system 100 comprising a rotary valve with a plurality of openings. Further, the respiratory system 100 includes a Y-shaped tube 118 for connecting the pressure generating sources 102, 104 to the interfacing assembly 106. However, it is evident to a person skilled in the art that any other appropriate tube known in the art can also be used in place of the Y-shaped tube.

Figure 3A:
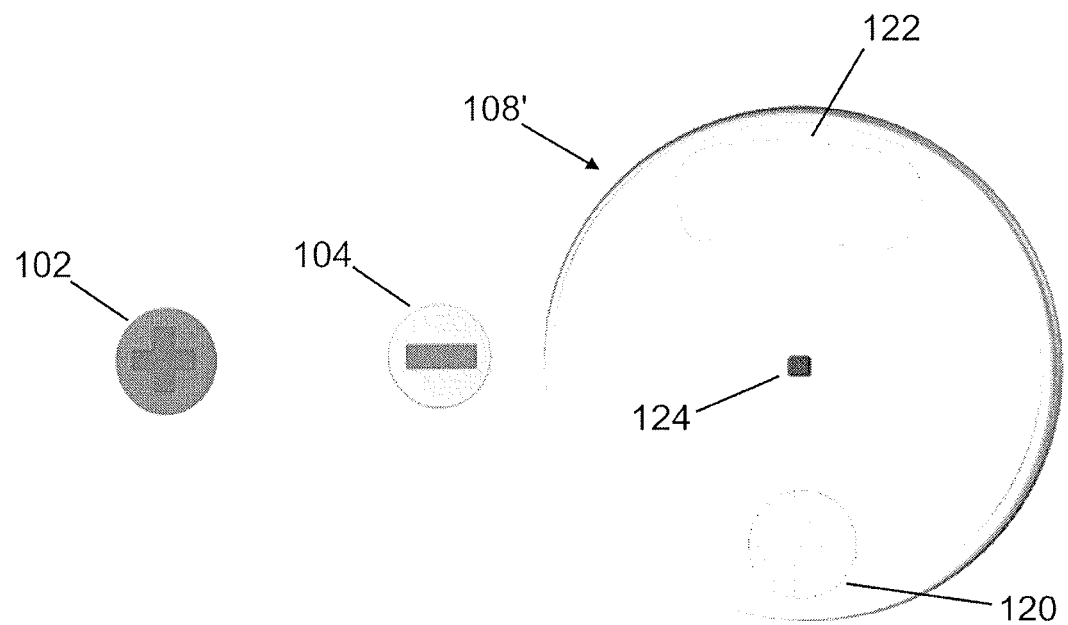
FIGS. 3a, 3b, 3c, 3d, 3e, 3f, 3g and 3h illustrate a plurality of rotary positions of a two opening rotary valve with respect to the positive and negative pressure generating sources in accordance with an embodiment of the present subject matter.
Figure 3B:
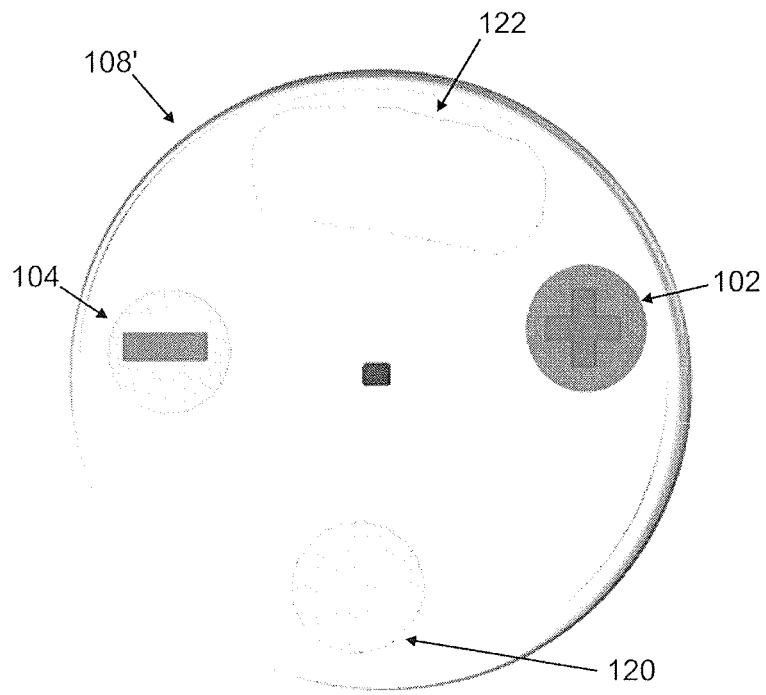

In an embodiment, the primary valve is a two opening rotary valve 108' comprising a thin disc having two openings fluidly connected to the first pressure generating source 102 and the second pressure generating source 104 to selectively allow flow of air from either pressure generating sources. The two opening rotary valve is operated by a single motor with its shaft attached to the center 124 of said valve. FIGS. 3a, 3b, 3c, 3d, 3e, 3f, 3g and 3h illustrate a plurality of rotary positions of a two opening rotary valve 108' with respect to the positive and the negative pressure generating sources in accordance with an embodiment of the present subject matter. The two opening rotary valve 108' is positioned between the pressure generating sources 102, 104 and the interfacing assembly 106 to selectively allow pressurized air from the respective pressure generating sources to the interfacing assembly 106. The two opening rotary valve includes a first opening 120 and a second opening 122 which can be in fluid connection with the positive and negative pressure generating sources respectively. The first opening 120 can be circular in shape and the second opening 122 can be either rectangular or elliptical in shape. However, the shape of first and second opening 122 is only illustrative and not limiting the present subject matter. Further, the size of the first and second opening 122 can be either same or different. The center 124 of the two-opening rotary valve is connected to a shaft (not shown) which enables the rotation of said valve. FIG. 3b illustrates the two opening rotary valve, wherein the interfacing assembly 106 is fluidly disconnected from the first and second pressure generating source. The 'first pressure generating source' of the present invention is also referred as the 'positive pressure generating source' and the 'second pressure generating source' is also referred as the 'negative pressure generating source' for the purpose of the present detailed description.

Figure 3C:
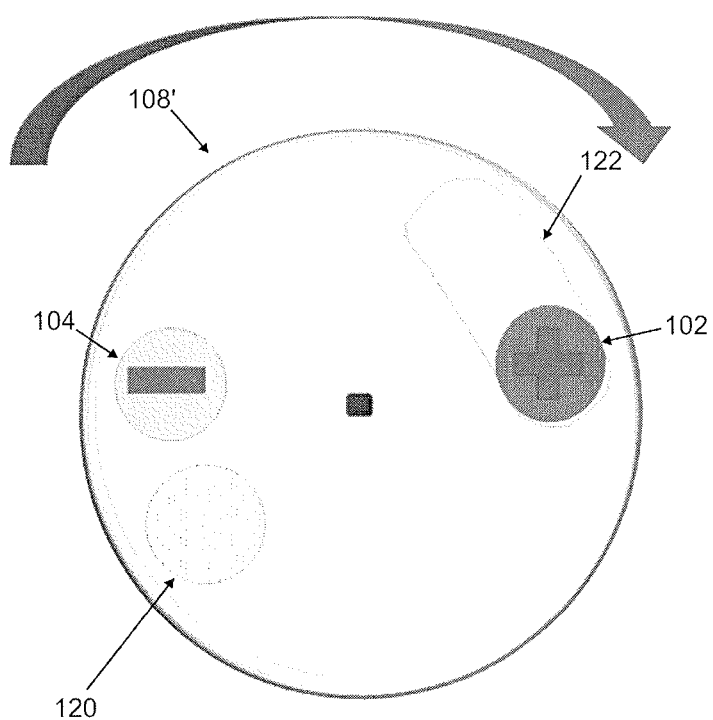

FIG. 3c illustrates a first position of the two opening rotary valve, wherein the interfacing assembly 106 is fluidly connected to the positive pressure generating source 102 through the second opening 122 and disconnected from the negative pressure generating source 104. In other words, only the negative pressure generating source 104 is completely blocked and the positive pressure generating source 102 completely overlaps with the second opening 122. Such an orientation is configured to generate only positive air flow or insufflation at the interfacing assembly 106.

Figure 3D:
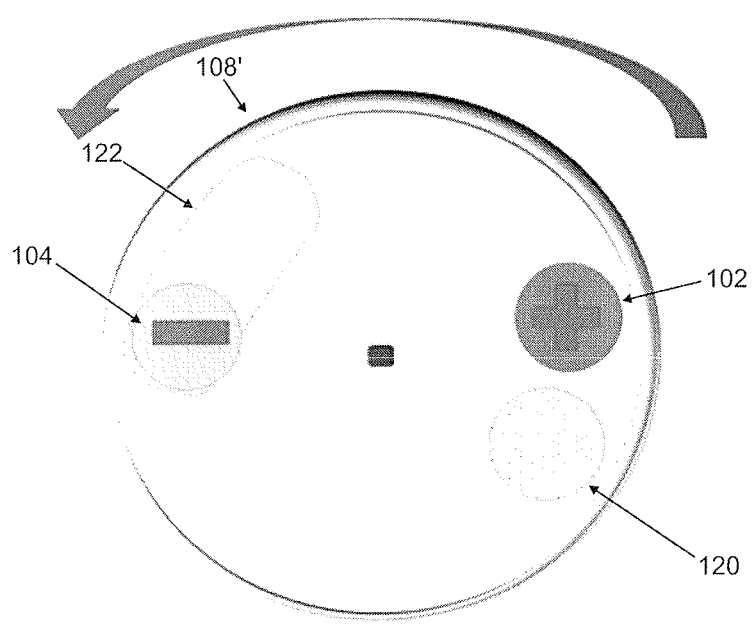

FIG. 3d illustrates a second position of the two opening rotary valve, wherein the interfacing assembly 106 is fluidly connected to the negative pressure generating source 104 through the second opening 122 and disconnected from the positive pressure generating source 102. In other words, only the positive pressure generating source 102 is completely blocked and the negative pressure generating source 104 completely overlaps with the second opening 122. Such an orientation is configured to generate only negative air flow or exsufflation at the interfacing assembly 106.

Figure 3E:
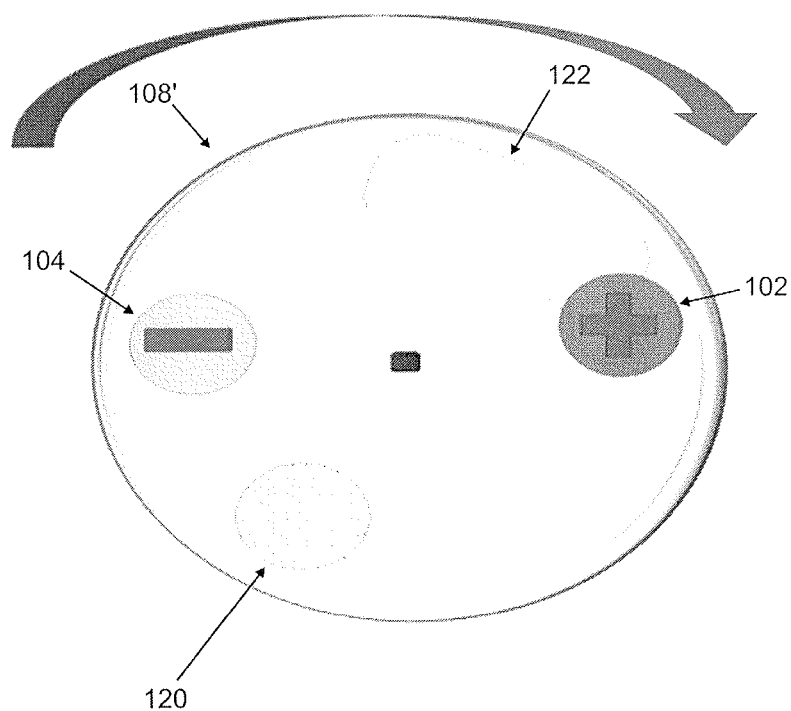

FIG. 3e illustrates a third position of the two opening rotary valve. This orientation allows partial positive pressurized flow from the positive pressure generating source 102 to the interfacing assembly 106. The negative pressure generating source 104 is fluidly disconnected from the interfacing assembly 106. The fourth position allows a variable displacement from said fourth position and is configured to impart oscillations on top of positive pressure airflow. However, it is evident to a person skilled in the art that the position shown in FIG. 3e is for illustration purpose only and in broader terms, such position refers to slight overlap of second opening 122 with the positive pressure generating source 102. Said overlap range can be any value between 1% and 99%, the first opening 120 is fluidly disconnected from both the pressure generating sources. The two opening rotary valve in said orientation allows the positive pressure generating source 102 to undergo a variable displacement to impart oscillations through the positive pressure air flow.

Figure 3F:
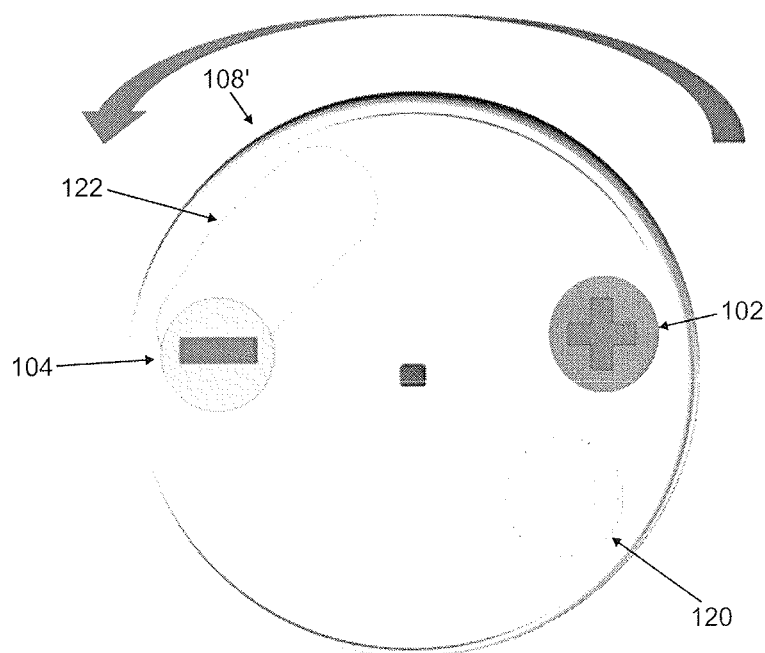

FIG. 3f illustrates a fourth position of the two opening rotary valve. This orientation allows partial negative pressurized flow from negative pressure generating source 104 to the interfacing assembly 106. The positive pressure generating source 102 is fluidly disconnected from the interfacing assembly 106. However, it is evident to a person skilled in the art that the position shown in FIG. 3f is for illustration purpose only and in broader terms, such position refers to slight overlap of second opening 122 with the negative pressure generating source 104. Said overlap can be any value between 1% and 99%, the first opening 120 is fluidly disconnected from both the pressure generating sources. The two opening rotary valve in said orientation allows the negative pressure generating source 104 to undergo a variable displacement to impart oscillations through the negative pressure air flow.

Figure 3G:
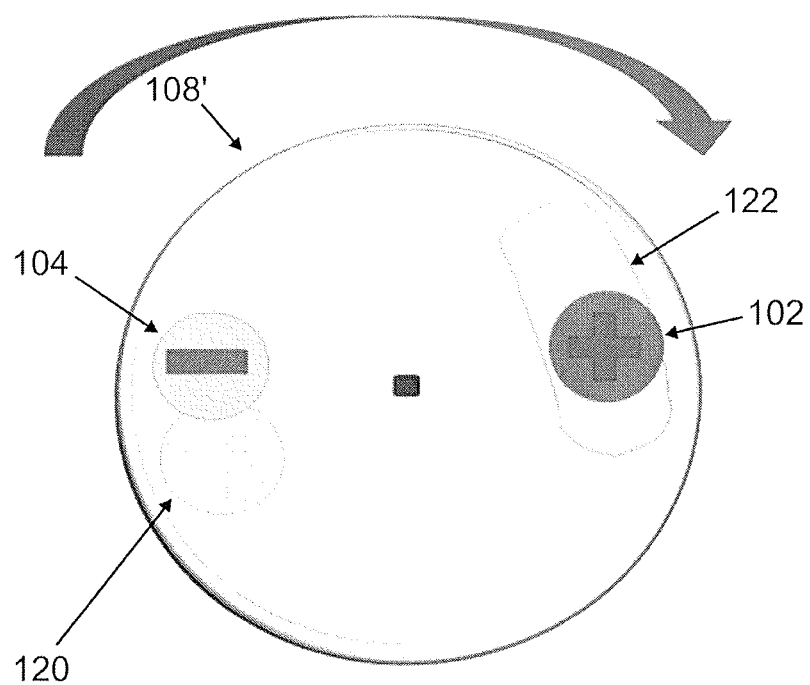

FIG. 3g illustrates a fifth position of the two opening rotary valve. In this position, the second opening 122 completely overlaps with the positive pressure generating source 102 and allows complete positive pressurized flow to the interfacing assembly 106. The negative pressure generating source 104 partially overlaps with the first opening 120 and allows partial negative pressurized flow from negative pressure generating source 104 to the interfacing assembly 106. However, it is evident to a person skilled in the art that the position shown in FIG. 3g is for illustration purpose only and in broader terms, the sixth position refers only to the second opening 122 completely fluidly connected to the positive pressure generating source 102 allowing positive pressurized flow to the interfacing assembly 106, and the first opening 120 fluidly partially overlaps with the negative pressure generating source 104. The two opening rotary valve in said orientation allows the negative pressure generating source 104 to undergo a variable displacement to impart oscillations through the negative pressure air flow. Further, said two opening rotary valve in said position also allows complete positive pressurized air flow or insufflation at the interfacing assembly 106.

Figure 3H:
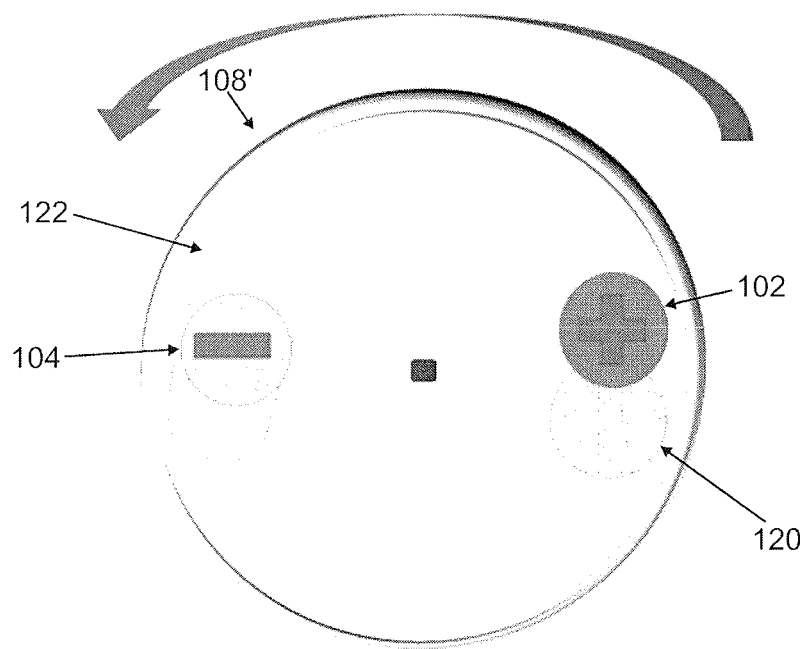

FIG. 3h illustrates a sixth position of the two opening rotary valve. In this position, the second opening 122 completely overlaps the negative pressure generating source 104 and allows complete positive pressurized flow to the interfacing assembly 106. The positive pressure generating assembly partially overlaps with the first opening and allows partial positive pressurized flow from positive pressure generating source 102 to the interfacing assembly 106. However, it is evident to a person skilled in the art that the position shown in FIG. 3h is for illustration purpose only and in broader terms, the seventh position refers only to the second opening completely fluidly connected to the negative pressure generating source 104 allowing negative pressurized flow to the interfacing assembly 106, and the first opening 120 fluidly partially overlaps with the positive pressure generating source 102. The two opening rotary valve in said orientation allows the positive pressure generating source 102 to undergo a variable displacement to impart oscillations through the positive pressure air flow. Further, said two opening rotary valve in said position also allows complete negative pressurized air flow or exsufflation at the interfacing assembly 106.

The respiratory system 100 described is capable of providing a multitude of therapies for respiratory patients. In operation, the control unit is configured to switch the two opening rotary valve between the first position (FIG. 3c) and the second position (FIG. 3d) which results in mechanical insufflation therapy. Further, alternate switching between completely blocked position (FIG. 3b) and third position (FIG. 3e) results in a oscillation of positively pressurized flow and alternating switching between completely blocked position (FIG. 3b) and fourth position (FIG. 3f) results in a oscillation of negatively pressurized flow. Amplitude of these oscillations is determined by how far the second opening and first opening 120 fluidly occlude the respective pressure generating sources. Furthermore, alternate switching between the first position (FIG. 3c) and the fifth position (FIG. 3g) results in oscillation through negatively pressured flow and alternate switching between second position (FIG. 3d) and sixth position (FIG. 3h) results in oscillation through positively pressured flow. The invention doesn't limit other possible combination of valves and orientations to generate secondary oscillations on top of primary oscillations described. It is to be noted that with the help of the additional secondary valve 110, secondary oscillations can be achieved on either on insufflation cycles or exsufflation cycles.

Figure 4A:
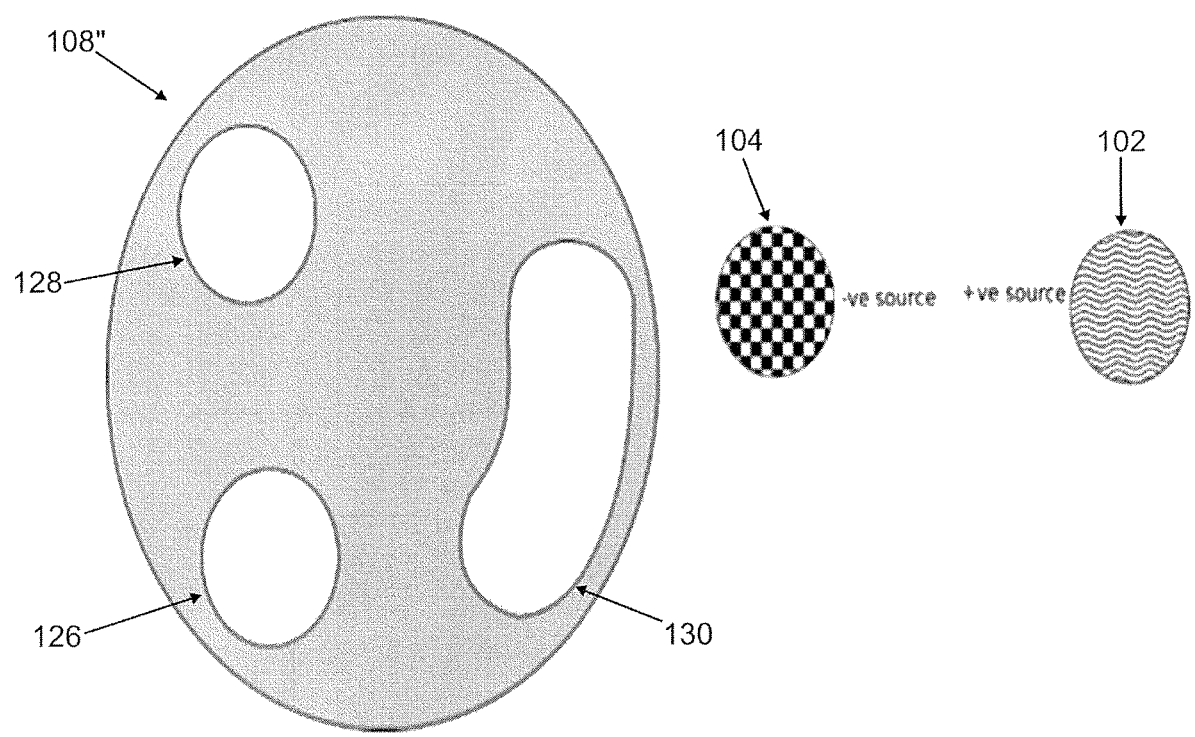
FIGS. 4a, 4b, 4c and 4d illustrate a plurality of rotary positions of a three opening rotary valve with respect to the positive and negative pressure generating sources in accordance with an embodiment of the present subject matter.
Figure 4B:
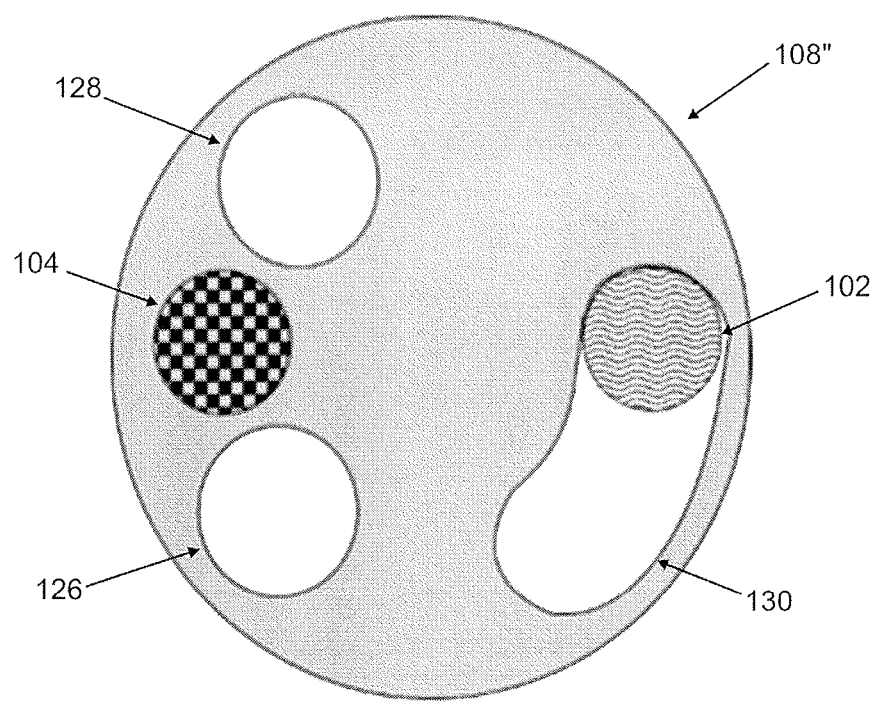

In an embodiment, the primary valve is a three-opening rotary valve 108" comprising a thin disc having three openings fluidly connected to the first pressure generating source 102 and the second pressure generating source 104 to selectively allow flow of air from either pressure generating sources. The disc is enclosed in a housing (not shown) with inlet and outlet ports corresponding to the negative and positive pressure generating sources. The three opening rotary valve is operated by a single stepper motor with its shaft attached to the center 124 of said valve. FIGS. 4a, 4b, 4c and 4d illustrate a plurality of rotary positions of a three opening rotary valve with respect to the positive and negative pressure generating sources in accordance with an embodiment of the present subject matter. The three opening rotary valve is positioned between the pressure generating sources and the interfacing assembly 106 to selectively allow pressurized air from the respective pressure generating sources to the interfacing assembly 106. The three opening rotary valve includes a first opening 126, a second opening 128 and a third opening 130 which can be in fluid connection with the positive and negative pressure generating sources. The first opening 126 and the second opening 128 can be circular in shape whereas the third opening 130 can be either rectangular or elliptical with straight sides. However, shape of the first, second and third opening 130 is only illustrative and not limiting the present subject matter. Further, the size of the first, second and third opening 130 can be either same or different. The center of the three opening rotary valve is connected with a shaft which enables the rotation of said valve. The first opening 126 is dedicated for negative pressure source. Upon rotation of the three opening rotary valve, the first opening 126 rotates simultaneously with the second opening 128 on opposing side to close the negative pressure generating source 104 while the positive pressure generating source 102 is made open due to the rotary motion of the disc. The second opening 128 when operated in conjunction with the first opening 126 in opposing side, opens and closes the positive pressure source in opposing phase to the first opening 126. Further, the third opening can oscillate the negative pressure generating source 104 from closed position while the second opening 128 keeps the positive pressure generating source 102 open due to its elongated shape. FIG. 4b illustrates a first position of the three opening rotary valve, wherein only positive pressure generating source 102 is open and overlaps completely with the second opening 128. The three opening rotary valve in said orientation allows insufflation through the respiratory system 100.

Figure 4C:
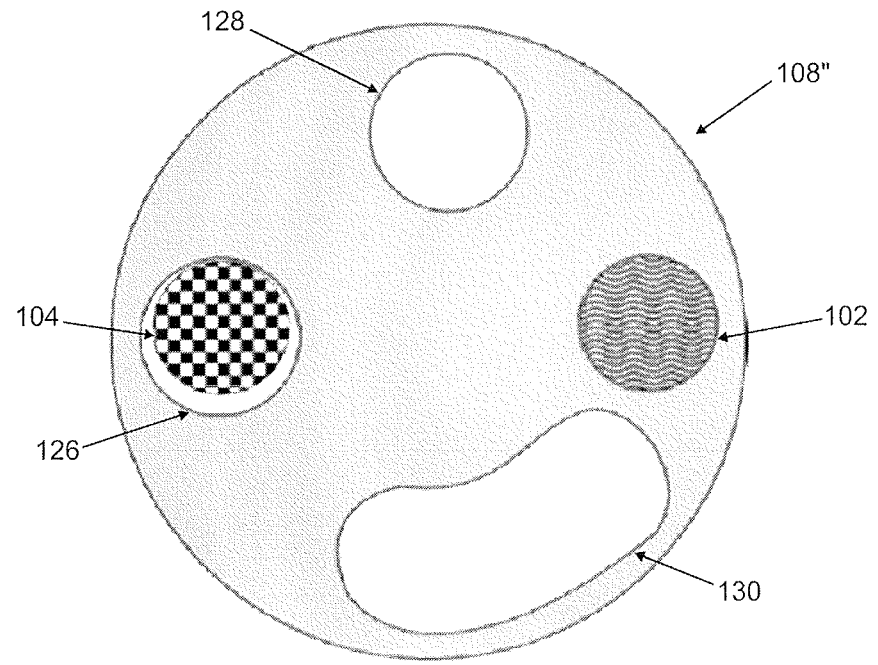
Figure 4D:
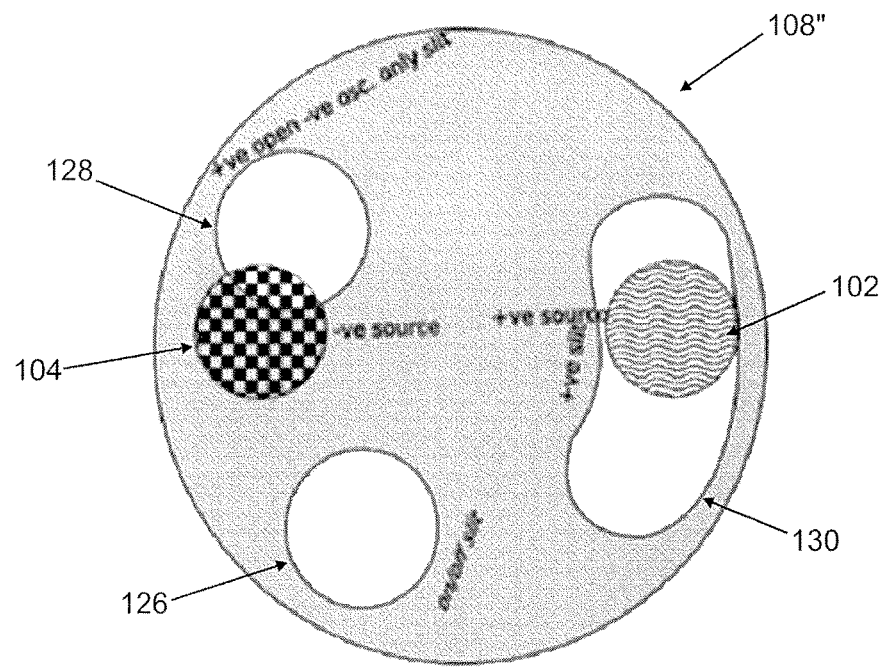

FIG. 4c illustrates a second position of the three opening rotary valve. In this position, only negative pressure generating source 104 is open and overlaps completely with the first opening 126. The three opening rotary valve in said orientation allows exsufflation through the respiratory system 100. This position can also be oscillated for both positive and negative source at high frequency. Further, FIG. 4d illustrates a third position of the three opening rotary valve wherein the third opening 130 completely overlaps with the positive pressure generating source 102 and the second opening 128 partially overlaps with the negative pressure generating source 104. Thus, the negative pressure generating source 104 oscillates and the positive pressure generating source 102 is completely open for insufflation. The invention doesn't limit other possible combination of valves and orientations to generate secondary oscillations on top of primary oscillations described. It is to be noted that with the help of additional secondary valve 110, secondary oscillations can be achieved on either on insufflation cycles or exsufflation cycles.

Figure 5A:
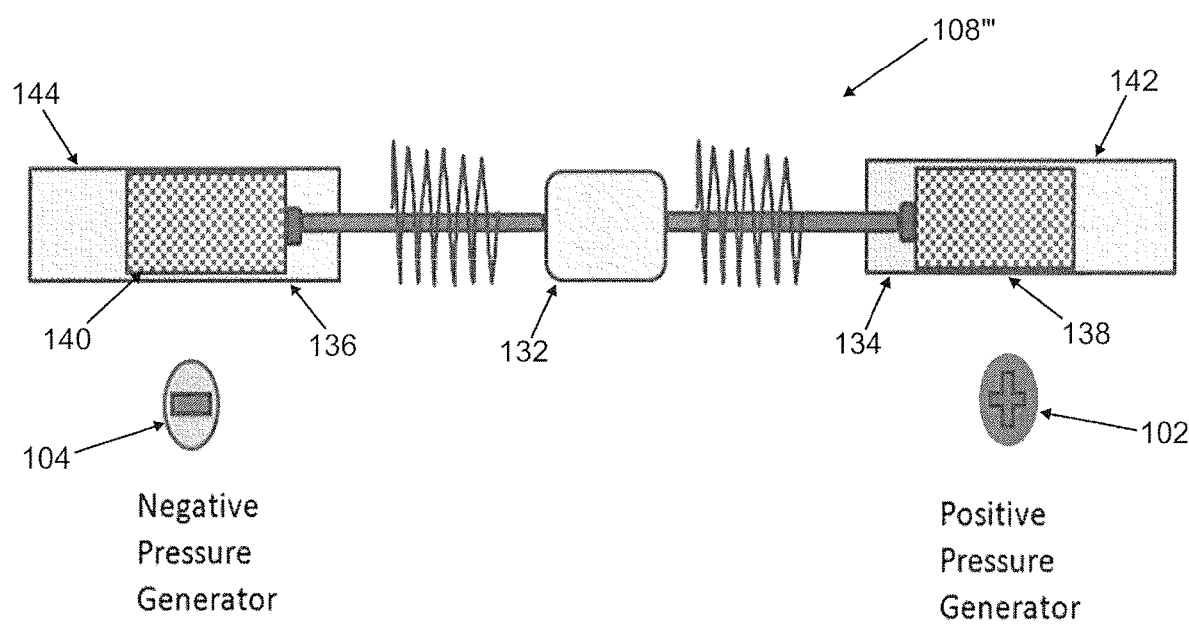
FIGS. 5a, 5b, 5c, 5d, 5e, 5f and 5g illustrates a plurality of positions of voice coil plungers of a voice coil valve with respect to the positive and negative pressure generating sources in accordance with an embodiment of the present subject matter.
Figure 5B:
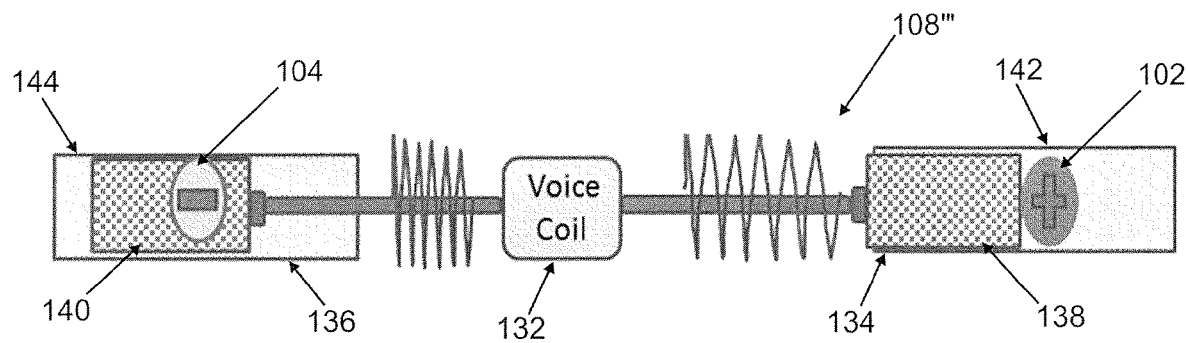

In an embodiment, the primary valve used to manipulate pressurized airflow is a voice coil based valve/voice coil valve. FIGS. 5a, 5b, 5c, 5d, 5e, 5f and 5g illustrate a plurality of positions of voice coil plungers of a voice coil valve 108''' with respect to the positive and negative pressure generating sources in accordance with an embodiment of the present subject matter. The voice coil valve 108''' can be used for mechanical insufflation and exsufflation process in combination with the pressure generating sources. The voice coil valve includes a voice coil 132 with a first plunger 134 corresponding to the positive pressure generating source 102 and a second plunger 136 corresponding to the negative pressure generating source 104. The first and second plungers 134, 136 extend on both sides of the voice coil 132 and are supported by leaf springs. Each of the ends of the first and second plungers 134, 136 includes a first strip 138 and a second strip 140 respectively. The first strip 138 is capable of covering the opening of positive pressure generating source 102 and the second strip 140 is capable of covering the opening of negative pressure generating source 104. The voice coil valve 108''' further includes a first air tight housing 142 for axial movement of the first plunger 134 and a second air tight housing 144 for axial movement of the second plunger 136. Further, the first and second housing include two inlet ports and two outlet ports corresponding to the positive pressure generating source 102 and the negative pressure generating source 104 respectively. FIG. 5b illustrates a first position of the voice coil valve with respect to the positive pressure generating source 102 and the negative pressure generating source 104. In this position, the first strip 138 does not cover the positive pressure generating source 102 and allows positive pressure air flow to the interfacing assembly 106. The second strip 140 completely covers the negative pressure generating source 104 and thus, the negative pressure airflow is fluidly disconnected from the interfacing assembly 106. It is to be noted that the voice coil construction is for illustration purpose only. Other variations are possible to extend or lessen the dimension of the plungers and other structures described here to get the similar waveforms at the patient interface.

Figure 5C:
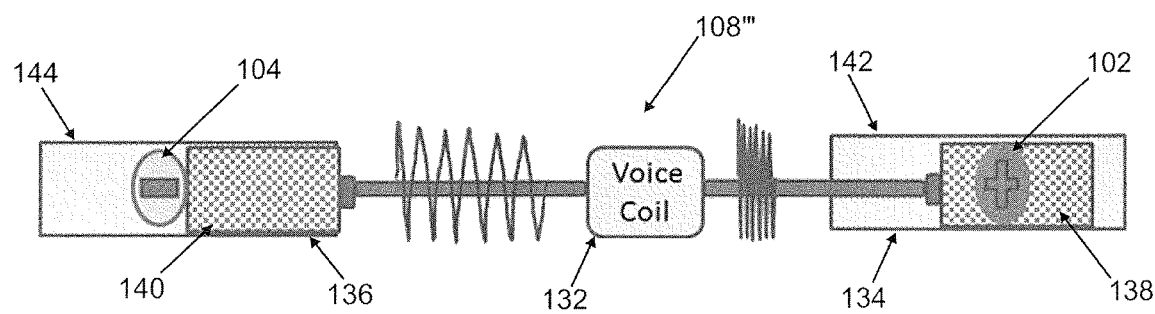

FIG. 5c illustrates a second position of the voice coil valve with respect to the positive pressure generating source 102 and the negative pressure generating source 104. In this position, the first strip 138 completely covers the positive pressure generating source 102 and the positive pressure air flow is disconnected from the interfacing assembly 106. The second strip 140 does not cover the negative pressure generating source 104 and thus allows negative pressure airflow to the interfacing assembly 106.

Figure 5D:
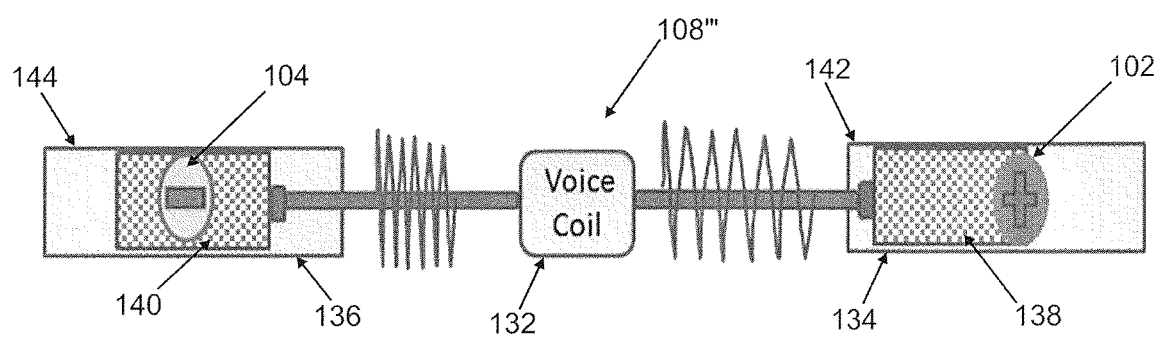

Further, FIG. 5d illustrates a third position of the voice coil valve with respect to the positive pressure generating source 102 and the negative pressure generating source 104. In this position, the first strip 138 partially covers the positive pressure generating source 102 and allows positive pressure airflow to the interfacing assembly 106. The second strip 140 completely covers the negative pressure generating source 104 and negative airflow is fluidly disconnected from the interfacing assembly 106. Alternate back and forth operation between the first position (FIG. 5b) and the third position (FIG. 5d) results in oscillation of positive pressure generating source/positive pressure airflow.

Figure 5E:
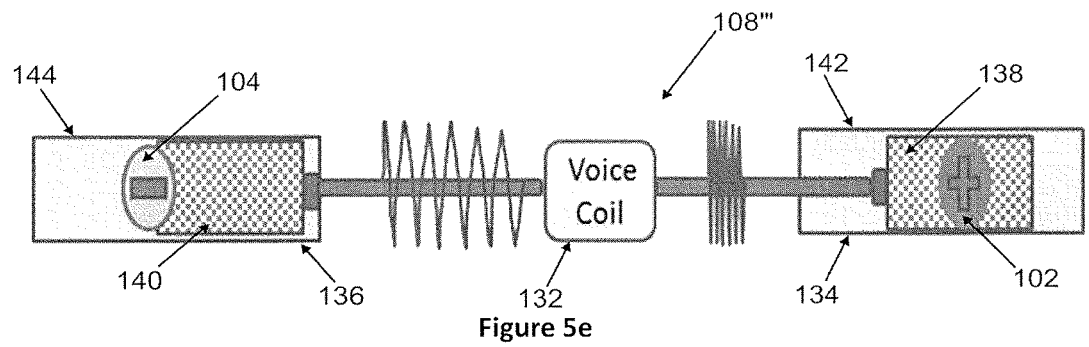

FIG. 5e illustrates a fourth position of the voice coil valve with respect to the positive pressure generating source 102 and the negative pressure generating source 104. In this position, the first strip 138 completely covers the first pressure generating source 102 and the positive pressure airflow is fluidly disconnected from the interfacing assembly 106. The second strip 140 partially covers the negative pressure generating source 104 and fluidly, partially, allows negative pressure airflow to the interfacing assembly 106. Alternate back and forth operation between the second position (FIG. 5c) and fourth position (FIG. 5e) results in oscillation of negative pressure generating source/negative pressure flow.

Figure 5F:
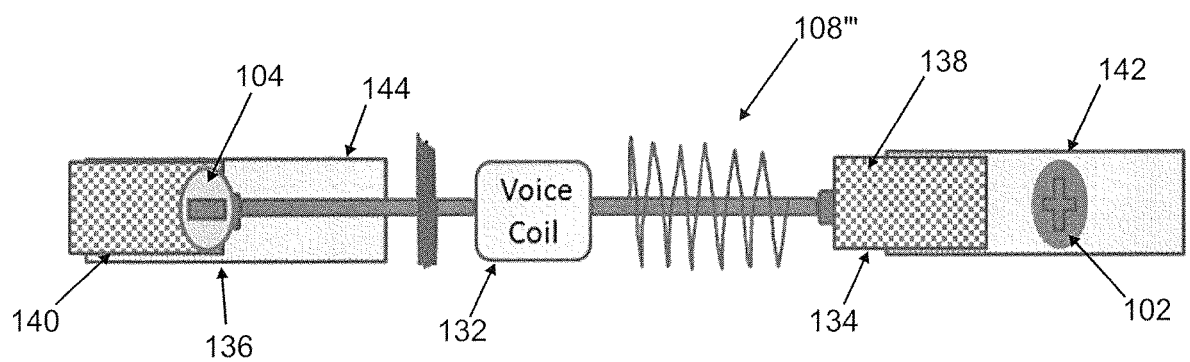

FIG. 5f illustrates a fifth position of the voice coil valve with respect to the positive pressure generating source 102 and the negative pressure generating source 104. In this position, the first strip 138 does not cover the first pressure generating source 102 and the positive pressure airflow is fluidly completely connected to the interfacing assembly 106. The second strip 140 partially covers the negative pressure generating source 104 and fluidly, partially, allows negative pressure airflow to the interfacing assembly 106. Alternate back and forth operation between the first position (FIG. 5b) and fifth position (FIG. 5f) results in oscillation of negative pressure flow while the respiratory system 100 is in insufflation phase.

Figure 5G:
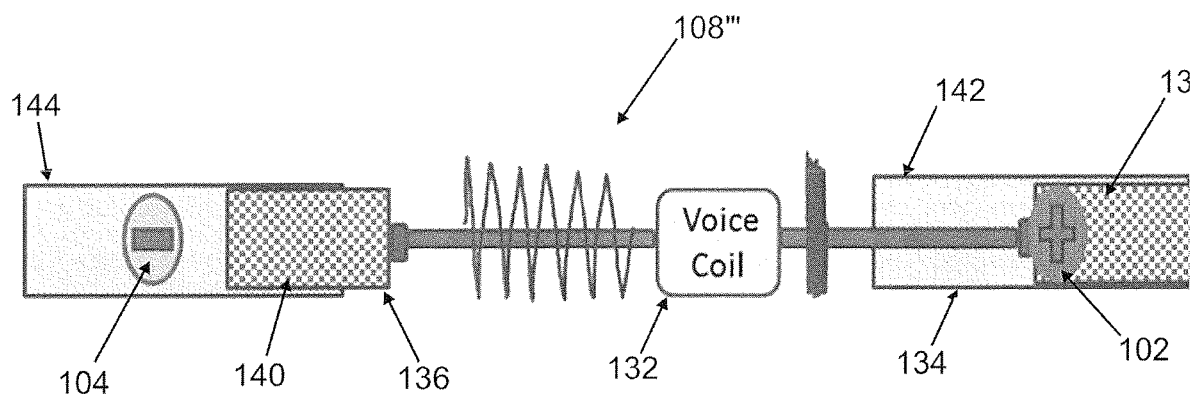

FIG. 5g illustrates a sixth position of the voice coil valve with respect to the positive pressure generating source 102 and the negative pressure generating source 104. In this position, the first strip 138 partially covers the first pressure generating source 102 and the positive pressure airflow is fluidly, partially, allows positive pressure airflow to the interfacing assembly 106. The second strip 140 does not cover the negative pressure generating source 104 and negative pressure airflow is fluidly completely connected to the interfacing assembly 106. Alternate back and forth operation between the second position (FIG. 5c) and sixth position (FIG. 5g) results in oscillation of positive pressure flow while device is in exsufflation phase.

In an embodiment, the respiratory system 100 further comprises a manifold/air router structure. The manifold/air router structure can be hollow cuboidal type, circular type, Y-shaped, cylindrical type or any other suitable manifold/air router structure type known in the art. However, it is evident to a person of ordinary skills in the art that the type of manifold/air router structure used does not limit the scope of the present disclosure. The primary valve 108 structure is in fluid connection with the interfacing assembly 106 through the manifold/air router structure. As with the rotary valve structure, the invention doesn't limit other possible combination of valves and orientations to generate secondary oscillations on top of primary oscillations described. It is to be noted that with the help of additional secondary valve 110, secondary oscillations can be achieved on either on insufflation cycles or exsufflation cycles.

As described hereinabove, the respiratory system 100 of the present subject matter provides a unique opportunity to address the present challenges. The respiratory system 100 can deliver multitude of functions to assist patient with neuromuscular issues to manage their secretion.

Although the invention has been described with reference to specific embodiments, this description is not meant to be construed in a limiting sense. Various modifications of the disclosed embodiments, as well as alternate embodiments of the invention, will become apparent to persons skilled in the art upon reference to the description of the invention. It is therefore, contemplated that such modifications can be made without departing from the spirit or scope of the present invention as defined.

I claim:

1. A respiratory system comprising:
   a patient interface unit configured to permit either a negative pressure airflow or a positive pressure airflow to a patient interface;
   a negative pressure generating source for generating negative pressure airflow that flows through the patient interface unit;
   a positive pressure generating source for generating positive pressure airflow that flows through the patient interface unit;
   a rotary valve comprising a disc having at least two openings, the rotary valve fluidly connected to said pressure generating sources;
   a first fluid connection, of the at least two openings on the rotary valve, for selectively blocking airflow from the positive pressure generating source; and
   a second fluid connection, of the at least two openings on the rotary valve, for selectively blocking airflow from the negative pressure generating source,
   wherein the first fluid connection and the second fluid connection have different shapes.

2. The respiratory system as claimed in claim 1, wherein said rotary valve at a first position, is configured to block negative pressurized airflow at the patient interface and allows the positive pressurized airflow to enter the patient interface,
   said rotary valve at a second position, configured to block the positive pressurized airflow at the patient interface and allows the negative pressurized airflow to enter the patient interface,
   said rotary valve at a third position, with a variable displacement from said third position configured to impart oscillations on top of positive pressure airflow,
   said rotary valve at a fourth position, with a variable displacement from said fourth position configured to impart oscillations on top of negative pressure airflow.

3. The respiratory system as claimed in claim 1, wherein said pressure generating sources are connected to the patient interface unit by a tube.

4. The respiratory system as claimed in claim 1, wherein the rotary valve comprises at least two or more openings of equal or varying sizes.

5. The respiratory system as claimed in claim 4, wherein the positive pressure generating source overlaps with either of said openings to allow positive air flow at the patient interface.

6. The respiratory system as claimed in claim 4, wherein the negative pressure generating source overlaps with either of said openings to allow negative air flow at the patient interface.

7. The respiratory system as claimed in claim 1, further comprising a control unit to control operation of said system.

8. The respiratory system as claimed in claim 1, wherein the rotary valve at a first position, is configured to block negative pressurized airflow at the patient interface and allows the positive pressurized airflow to enter the patient interface;
   said rotary valve at a second position, is configured to block the positive pressurized airflow at the patient interface and allows the negative pressurized airflow to enter the patient interface;
   said rotary valve at a third position, with a variable displacement from said third position configured to impart oscillations on top of positive pressure airflow;
   said rotary valve at a fourth position, with a variable displacement from said fourth position configured to impart oscillations on top of negative pressure airflow.

9. The respiratory system as claimed in claim 1, wherein the positive pressurized airflow ranges from 1 to 100 cmh20 as per the set parameters.

10. The respiratory system as claimed in claim 1, wherein the negative pressurized airflow ranges from −1 to −100 cmh20 as per the set parameters.

11. A method of performing a mechanical inexsufflation therapy comprising:
    generating positive pressure airflow/insufflation from a positive pressure generating source to a patient's interface/lung through a rotary valve comprising a disc having at least two openings, wherein the at least two openings have different shapes, wherein a first position of the rotary valve selectively prevents negative pressurized airflow at the patient's interface/lung, and allows the positive pressure airflow to enter the patient's interface/lung through a first opening of the at least two openings;

generating a negative pressure airflow/exsufflation by using a negative pressure generating source along the patient's interface/lung by using said rotary valve's second position, wherein the second position of the valve selectively prevents positive pressure airflow from entering the patient's interface/lung and allows the negative pressure airflow to enter the patient interface/lung through a second opening of the at least two openings;

generating oscillation, either during insufflation by oscillating positive airflow or during exsufflation by oscillating negative airflow, by back and forth switching of the rotary valve from a third position to a fourth position.

12. The method of performing a mechanical inexsufflation therapy as claimed in claim 11, wherein switching the rotary valve from first position to second position or second position to first position is based on pre-determined time or pressure or volume parameters.

13. The method of performing a mechanical inexsufflation therapy as claimed in claim 11, wherein the positive pressurized flow ranges from 1 to 100 cmh20 as per the set parameters.

14. The method of performing a mechanical inexsufflation therapy as claimed in claim 11, wherein the negative pressurized flow ranges from −1 to −100 cmh20 as per the set parameters.

15. The method of performing a mechanical inexsufflation therapy as claimed in claim 11, wherein generating pressurized airflows at the patient interface comprises a defined sequence:

positive pressure airflow, followed by positive pressured airflow of higher value, followed by negative pressure airflow.

16. A respiratory system comprising:
a patient interface unit configured to permit either a negative pressure airflow or a positive pressure airflow to a patient interface;
a negative pressure generating source for generating negative pressure airflow that flows through the patient interface unit;
a positive pressure generating source for generating positive pressure airflow that flows through the patient interface unit;
a rotary valve structure, comprising a disc having at least two openings, fluidly connected to said pressure generating source airflow paths for selectively blocking and unblocking airflow from either of the said pressure generating sources, wherein the at least two openings have different shapes; and
a second valve structure fluidly connected to a positive pressure airflow path and to a negative pressure airflow path to generate oscillations to said pressurized airflows.

17. The respiratory system as claimed in claim 16, wherein said rotary valve at a first position, blocks the negative pressure airflow at the patient interface and allows the positive pressure airflow to enter the patient interface;
said rotary valve at a second position, blocks the positive pressure airflow at the patient interface and allows the negative pressure airflow to enter the patient interface;
said rotary valve at a third position with a variable displacement from said third position can impart pressure oscillations during positive pressure airflow;
said rotary valve at a fourth position with a variable displacement from said fourth position can impart pressure oscillations during negative pressure airflow; and
said second valve at a first position with a variable displacement from said first position can impart pressure oscillations in either of pressurized airflow paths, depending on the location of the second valve.

18. The respiratory system as claimed in claim 16, wherein said second valve structure, operationally can change its position from one location to other, either inside the positive pressure path or inside the negative pressure path to generate oscillations on respective pressured airflows.

19. The respiratory system as claimed in claim 16, further comprising a control unit to control the operation of said system.

20. The respiratory system as claimed in claim 19, wherein the control system is configured to generate insufflation and exsufflation waveforms by only operating the said rotary valve.

21. The respiratory system as claimed in claim 16, wherein the pressure generating sources are connected to the patient interface unit by a tube.

* * * * *